United States Patent
Jonsson et al.

(10) Patent No.: US 7,384,543 B2
(45) Date of Patent: Jun. 10, 2008

(54) CIRCUIT FOR EXTRACORPOREAL BLOOD TREATMENT AND FLOW-INVERTING DEVICE UTILIZED THEREIN

(75) Inventors: Lennart Jonsson, Furulund (SE); Mattias Holmer, Lund (SE); Per Hansson, Lund (SE)

(73) Assignee: Gambro Lundia AB, Lund (SE)

( * ) Notice: Subject to any disclaimer, the term of this patent is extended or adjusted under 35 U.S.C. 154(b) by 538 days.

(21) Appl. No.: 10/976,416

(22) Filed: Oct. 29, 2004

(65) Prior Publication Data

US 2005/0145549 A1 Jul. 7, 2005

Related U.S. Application Data

(60) Provisional application No. 60/515,691, filed on Oct. 31, 2003.

(51) Int. Cl.
*B01D 35/02* (2006.01)
(52) U.S. Cl. .......................... 210/97; 210/136; 604/6.1
(58) Field of Classification Search ................ 210/97, 210/136, 646; 422/24; 604/6.16, 6.1, 6.09, 604/6.11, 4.01; 137/247.17, 247.27, 597
See application file for complete search history.

(56) References Cited

U.S. PATENT DOCUMENTS

| | | |
|---|---|---|
| 4,885,087 A | 12/1989 | Kopf |
| 5,058,416 A | 10/1991 | Engelhardt et al. |
| 5,605,630 A | 2/1997 | Shibata |
| 5,830,365 A | 11/1998 | Schneditz |
| 5,894,011 A | 4/1999 | Prosl et al. |
| 6,177,049 B1 | 1/2001 | Schnell et al. |
| 6,189,388 B1 | 2/2001 | Cole et al. |
| 6,308,737 B1 | 10/2001 | Krivitski |
| 6,319,465 B1 | 11/2001 | Schnell et al. |
| 6,596,234 B1 | 7/2003 | Schnell et al. |
| 6,743,193 B2 * | 6/2004 | Brugger et al. ............. 604/6.1 |
| 2001/0031222 A1 | 10/2001 | Schnell et al. |
| 2003/0018290 A1 | 1/2003 | Brugger et al. |
| 2003/0138348 A1 | 7/2003 | Bell et al. |

FOREIGN PATENT DOCUMENTS

WO  WO 00/24440  5/2000

OTHER PUBLICATIONS

International Search Report for International Application No. PCT/IB2004/003394, undated.
Shinmoto, K. et al., "Fluid Passage Change-Over Apparatus for Medical Treatment", European Patent Abstract of EP 1106191, Jun. 13, 2001.
Mercadal, L. et al., "Determination of Access Blood Flow from Ionic Dialysance: Theory and Validation", Kidney International, vol. 56, pp. 1560-1565, (1999).
Paul G. Sakiewicz, et al., "Introduction of a Switch that Can Reverse Blood Flow Direction On-Line during Hemodialysis" *ASAIO Journal*, vol. 46, No. 4, Jul. 2000, pp. 464-468.
Supplemental International Search Report for International Application No. PCT/IB2004/003394, undated.

* cited by examiner (Continued)

*Primary Examiner*—Terry K Cecil
(74) *Attorney, Agent, or Firm*—Finnegan, Henderson, Farabow, Garrett & Dunner, L.L.P.

(57) ABSTRACT

A circuit is disclosed for extracorporeal blood treatment in which a flow-inverting device is interposed between a blood treatment unit and a blood pump placed on an artery branch connected with a vascular access of a patient. The flow-inverting device allows the blood flow within the filtering unit to be kept unchanged even following an inverted circulation in the patient-side artery and vein branches controlled by the blood pump.

12 Claims, 10 Drawing Sheets

CIRCUIT FOR EXTRACORPOREAL BLOOD TREATMENT AND FLOW-INVERTING DEVICE UTILIZED THEREIN

This application claims the benefit of U.S. Provisional Application No. 60/515,691 filed on Oct. 31, 2003, the contents of which are incorporated herein by reference.

FIELD AND BACKGROUND OF THE INVENTION

The present invention relates to a circuit for extracorporeal blood treatment and the relevant device for flow inversion utilised therein.

It is known that during extracorporeal blood treatment the patient's vascular system is connected to a machine or unit for blood treatment, a dialysis machine, for example.

Connection to the machine creates a circuit in which the blood is drawn from the patient through a needle or other vascular access device connected to the patient itself; the blood is caused to circulate through the unit operating the appropriate treatments on the blood and is then returned to the patient through a return line and a corresponding needle or other access also connected to the patient's vascular system.

The interface between the machine and patient is made up of the vascular access from which the blood to be treated is drawn and to which the treated blood is caused to come back to the human body. It is to be noted that in treatments of the recurring type such as dialytic treatments on chronic patients, a relatively high blood flow in the extracorporeal circuit is required. For the purpose, either needles are used that are fitted in an arteriovenous aneurysm (or shunt) or catheters are used that are implanted into portions of the cardiovascular system where the blood flow is sufficiently high so as to ensure a high drawing capability of the blood to be treated.

It is therefore apparent that a decrease in the performance of the vascular access may represent a serious problem for the patient and therefore the vascular access must be periodically monitored to ensure an optimal functional character of same.

For the above and other purposes some parameters relating to the vascular access are often required to be measured.

One of the different parameters of interest is represented by the real flow passing through the access from which the blood is drawn and then introduced again into the patient's body.

It is in fact apparent that, if due to a degradation of the arteriovenous aneurysm for example (that may be due to the most different causes such as formation of stenosis, collapsing of the vascular walls or others), there is a decrease in the blood flow therein, the dialysis machine will be able to draw a lower amount of blood which will bring about a worsening in the treatment efficiency.

In general, for measuring some of the above mentioned parameters relating to the vascular access, the real aneurysm flow for example, there is a requirement of an inversion between the blood suction point and the blood delivery point at the vascular access.

It is apparent that carrying out this operation manually, i.e. by slipping the respective needles off and inverting suction with delivery in the patient, involves a great trouble for the patient, is time-consuming and as a matter of fact undermines reliability of the measurement of these parameters that are also partly linked to quickness in the inversion.

It is also to be noted that once the blood has been drawn from the patient, it is circulated in a treatment unit that is generally set to enable a counter-current exchange at the inside thereof between the blood to be treated and the dialysis liquid.

In other words, for a good operation of the dialysis machine, maintenance of a hydraulic counter current condition is required within the filtering unit.

To solve the above mentioned problems, appropriate devices to invert the suction and delivery lines at the vascular access have been recently spread, that do not require physical disconnection of the circuit lines for extracorporeal blood treatment from the vascular accesses.

Devices capable of enabling flow inversion at the patient-side suction and delivery branches, while keeping the circulation flow within the filtering unit unchanged have been also developed.

The U.S. Pat. No. 6,308,737 (Krivitski) discloses an inverter device interposed between the vascular access to the patient and the blood pump, and the dialyser capable of enabling a flow inversion in the blood circuit portion directly in communication with the patient's vascular system while keeping the extracorporeal blood flow within the dialyser unchanged.

The inverter in particular comprises a deformable chamber provided with a plurality of doors.

By deforming the chamber along a predetermined direction, a fluid communication between the pre-established doors is created while a fluid communication between other doors is prevented.

In particular, by suitably studying the connections of the extracorporeal blood circuit with the chamber doors and the deformations to be imposed to the chamber itself a flow inversion as above stated is obtained.

The U.S. Pat. No. 5,894,011 (Prosl) too discloses a device for flow inversion in haemodialysis apparatus. This device comprises two discs such interconnected that they can rotate relative to each other without separating. The two discs have appropriate fluid accesses, those of one disc being susceptible of connection with the blood lines directly associated with the patient and those of the other disc being susceptible of direct connection with the bloodlines in fluid communication with the filtering unit.

The two discs can take at least two relative angular positions; in a first position they enable passage of the blood flow in a first direction of direct circulation, in the other position (in which they are rotated relative to each other) they allow an inverted circulation flow in the circuit.

In particular in the second inverted configuration the blood suction line from the patient in the first position becomes the delivery line and correspondingly, the delivery line of the first position becomes the suction line in the second position.

The U.S. Pat. Nos. 6,177,049 and 6,319,465 (Schnell) disclose two further typologies of flow inverting valves both to be positioned between the vascular accesses to the patient and the blood pump and filtering unit.

The first patent teaches use of a fixed external valve body to the inside of which an appropriate insert is connected which is capable of being moved between a first direct-circulation configuration and a second reverse circulation configuration, as shown in FIGS. 1 and 2 of this patent.

In particular, in the second reverse-circulation condition the suction line and delivery line at the vascular access to the patient are inverted with each other with respect to the first direct-flow condition.

The second patent too shows a valve capable of exactly performing the same functions as the first patent, this valve being however made up of two halves coupled with each other so that they have a degree of freedom in rotation and, through mutual rotation of the two halves, a first direct-flow condition and a second reverse-flow condition are obtained at the vascular access to the patient.

A further device for flow inversion in accordance with the U.S. Pat. No. 5,605,630 (Shibata) is also known.

However this device is not used to invert the circulation flow at the vascular accesses to the patient, but to enable flow inversion within the filtering unit. In other words, the blood flow is inverted within the filtering unit intermittently and simultaneously the flow of the dialysis liquid is inverted within the same in such a manner that counter-current conditions are maintained therein. The above is carried out for quite different purposes from those of the present invention, i.e. to avoid blood clotting within the filter for dialysis. All the patented devices briefly mentioned above however appeared to be susceptible of improvements under different points of view.

SUMMARY OF THE INVENTION

Accordingly, it is an object of the present invention to overcome some operating limits of the known art by providing a circuit for extracorporeal blood treatment and a device for flow inversion to be used therein that represent an alternative to the devices hitherto known.

It is a secondary aim of the invention to provide a circuit for extracorporeal blood treatment in which a flow inversion can be obtained at the vascular accesses to the patient by an inversion of the thrust exerted by the blood pump and that is also capable of maintaining optimal counter-current conditions within the blood treatment unit.

It is a further aim of the invention to provide a circuit and a device for flow inversion capable of automatically maintaining the blood flow within the filtering unit constant even following inversion of the flow at the vascular accesses to the patient.

It is then an auxiliary aim of the invention to provide a device for flow inversion of different structure and conception as compared with the devices hitherto on the market, which is cheap and very reliable.

The foregoing and further aims, that will become more apparent in the course of the present description, are substantially achieved by a circuit for extracorporeal blood treatment and by the device for flow inversion utilised therein, in accordance with the features set out in the appended claims.

Further features and advantages will be best understood from the detailed description of a preferred, but not exclusive embodiment of a circuit for extracorporeal blood treatment in accordance with the present invention. This description will be carried out hereinafter with reference to the accompanying drawings, given by way of non-limiting example, in which:

DESCRIPTION OF THE PREFERRED EMBODIMENTS

Figure 1:
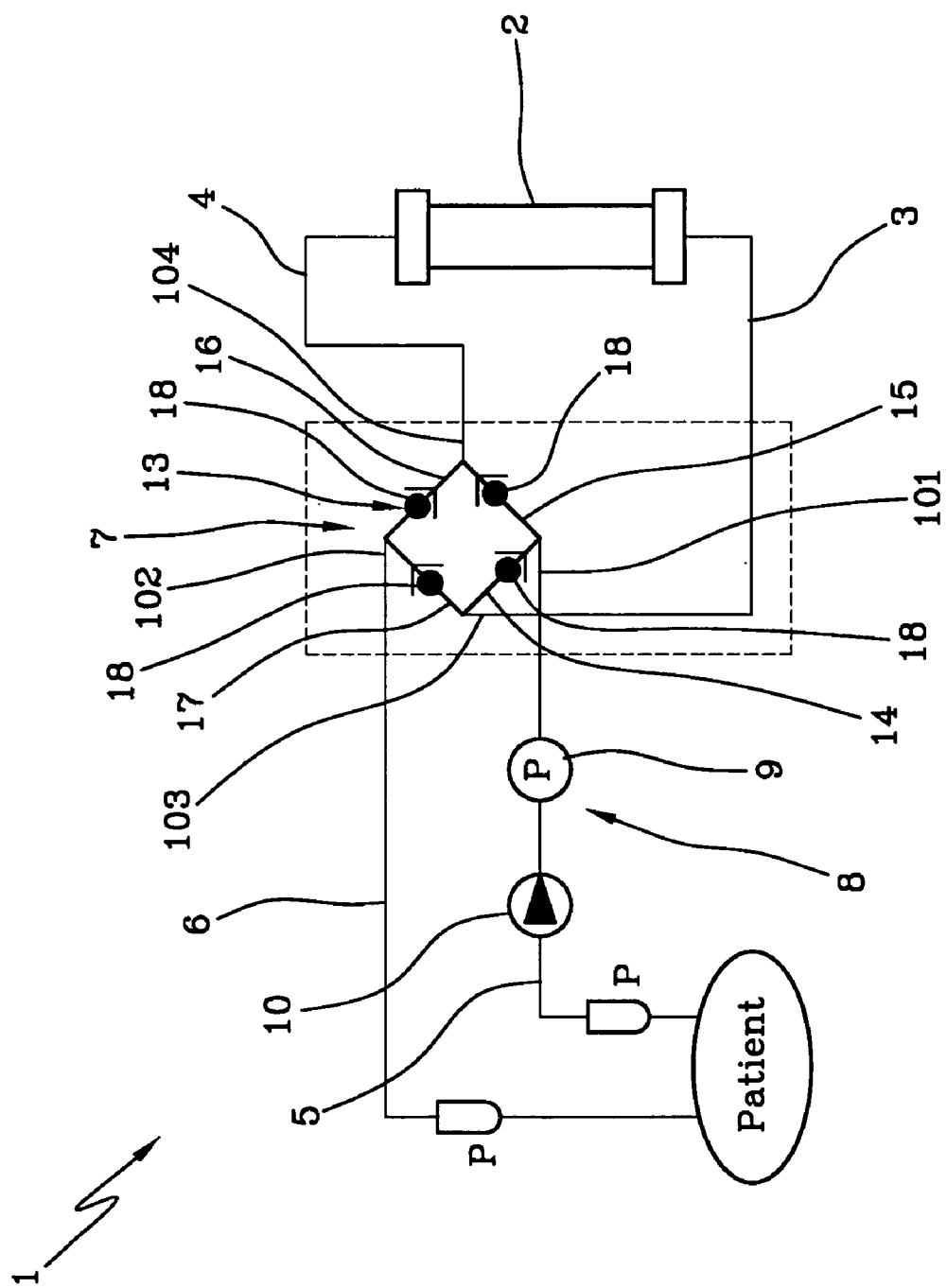
FIG. 1 is a diagrammatic view of a circuit for extracorporeal blood treatment in accordance with the present invention.

With reference to the drawings, a circuit for extracorporeal blood treatment in accordance with the present invention has been generally identified by reference numeral 1.

As can be noticed from the accompanying drawings, the circuit first of all comprises at least one blood-treatment unit 2 which may consist of a common filter for dialysis, for example. The blood treatment unit may equivalently comprise a plasma filter, an hemofilter or an hemodiafilter.

As can be viewed, there is the presence of at least one unit-side artery branch 3 entering the blood treatment unit 2 and at least one unit-side vein branch 4 exiting such a component.

The circuit also involves at least one patient-side artery branch 5 and at least one patient-side vein branch 6 designed to be brought into fluid connection with a vascular access of a patient to be submitted to treatment. The above mentioned unit-side artery and vein branches 3, 4 and patient-side artery and vein branches 5, 6 are interconnected with each other by interposition of a device for flow inversion (identified by 7 in the figures) capable of enabling different operating conditions of the circuit, as better clarified in the following.

Also present is movement means 8 capable of generating an extracorporeal blood flow within the circuit. In a first embodiment (FIGS. 1-3) this movement means 8 will be generally active on the patient-side artery branch 5 (even if it is obviously possible to position this means on the patient-side vein branch 6 too); anyway the movement means 8 can generally comprise at least one blood pump 9, a peristaltic pump for example of known type and presently widely used for applications in this sector. Of course other kind of pumps could be used in principle.

Obviously, two or more pumps may be provided for one or the other of the patient-side branches (or for other parts of the hydraulic circuit) and also the movement means 8 could consist of pumps of any nature such as positive-displacement pumping means as well.

From a structural point of view the flow-inverting device 7 has at least four accesses 101, 102, 103 and 104 designed to be brought into fluid connection with said patient-side and unit-side artery and vein branches.

In particular, the first access 101 is connected with the patient-side artery branch 5, the second access 102 is connected with the patient-side vein branch 6, the third access 103 is connected with the unit-side artery branch 3, whereas the fourth access 104 is connected with the unit-side vein branch 4.

In the first embodiment, each of said accesses is connected by appropriate connecting lines 14, 15, 16, 17 to at least two other accesses of the device.

Figure 2:
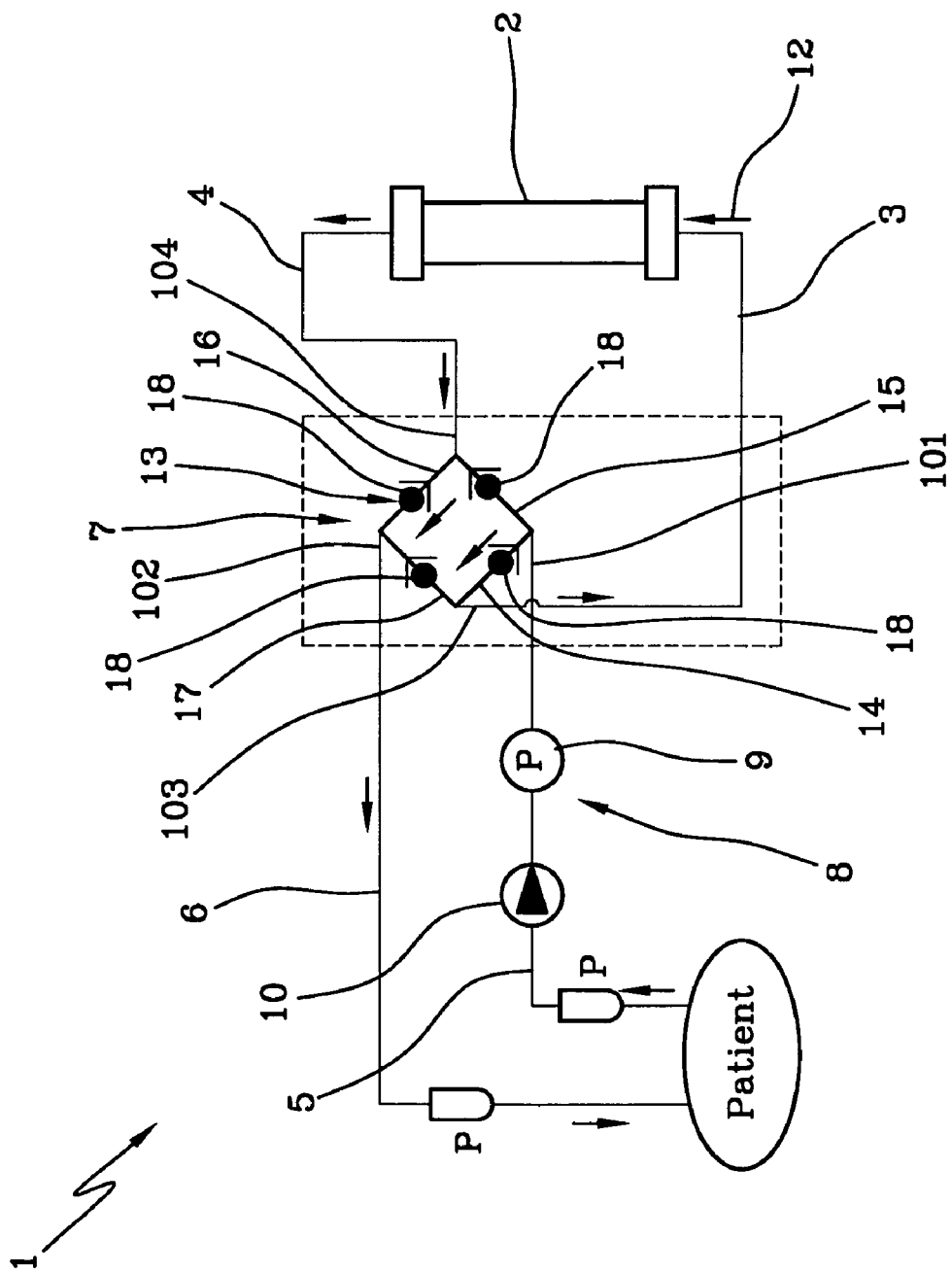
FIG. 2 shows the circuit in FIG. 1 in a first direct operating condition.
Figure 3:
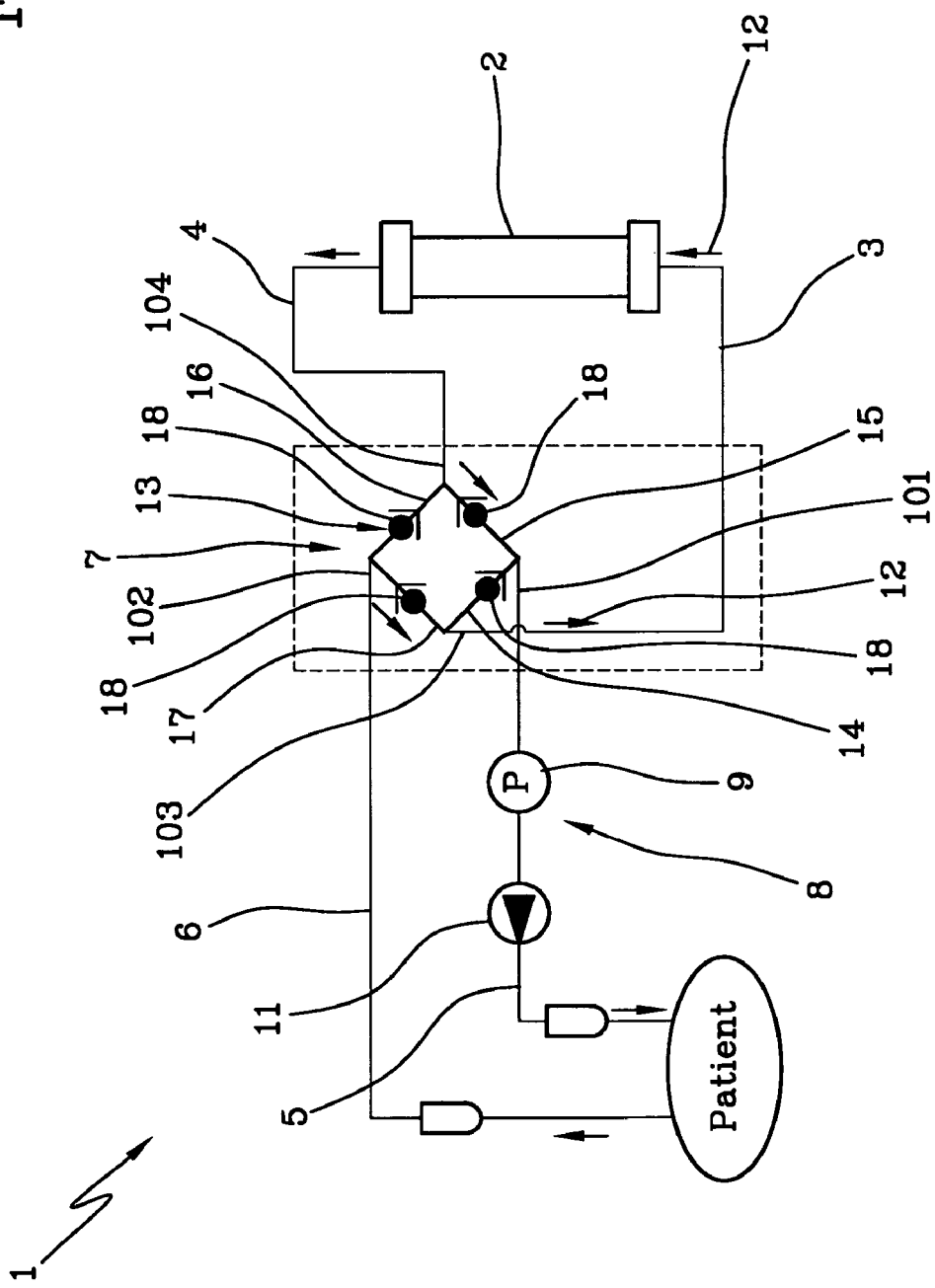
FIG. 3 shows the circuit in FIG. 1 in a second inverted operating condition.

As viewed from the accompanying FIGS. 1-3, the first connecting line 14 brings the first access 101 into fluid communication with the third access 103, the second connecting line 15 brings the first access 101 into fluid communication with the fourth access 104, the third connecting line 16 brings the second access 102 into fluid communication with the fourth access 104, whereas the fourth connecting line 17 brings the second access 102 into fluid communication with the third access 103.

In other words and as better clarified in the following when operation of the circuit is explained, the first access 101 can be selectively brought into communication with either the third access 103 or the fourth access 104, whereas the second access 102 can be selectively brought into fluid communication with either the fourth access 104 or the third access 103.

Figure 4:
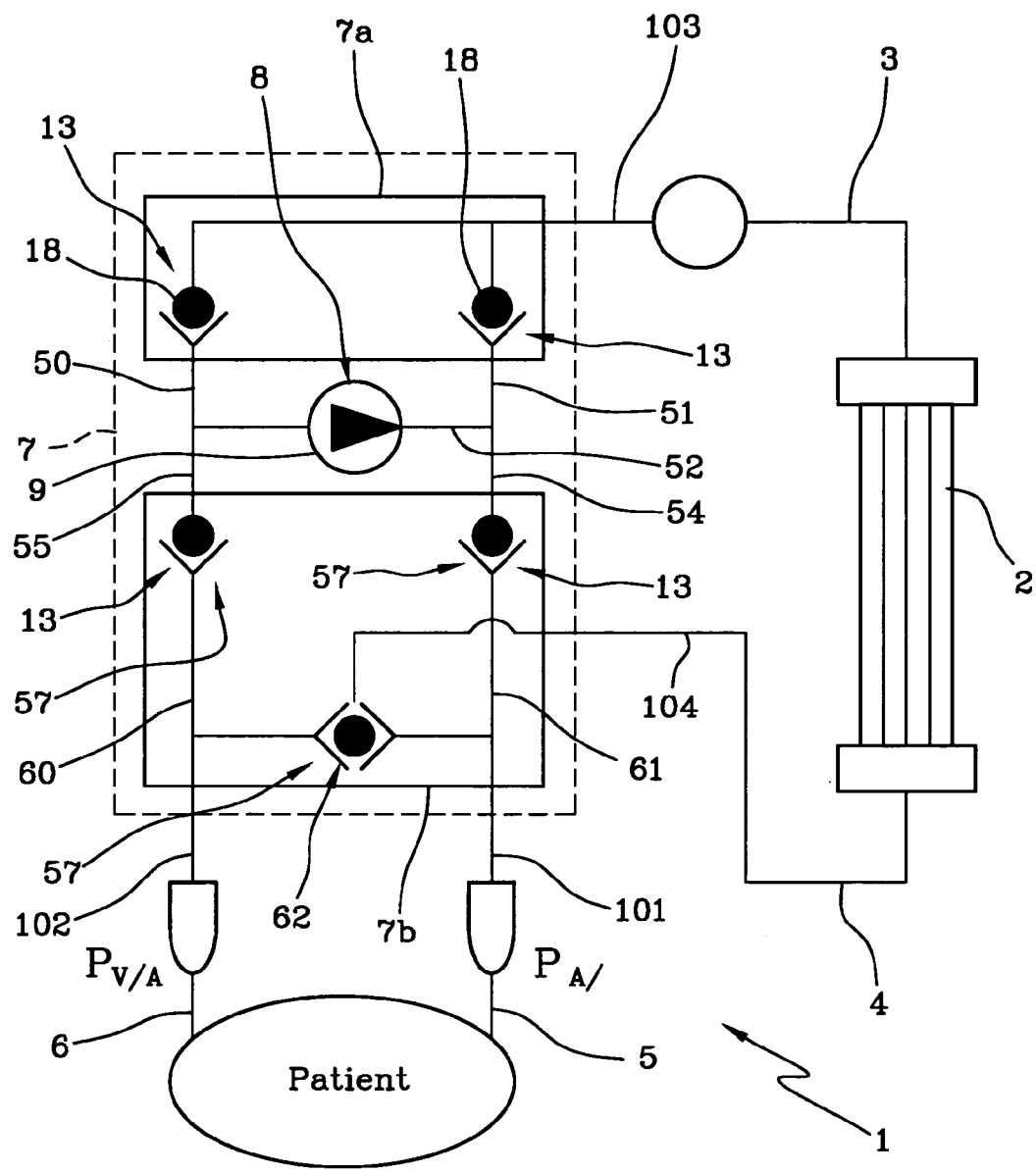
FIG. 4 is a diagrammatic view of a second circuit for extracorporeal blood treatment in according with the present invention.
Figure 7:
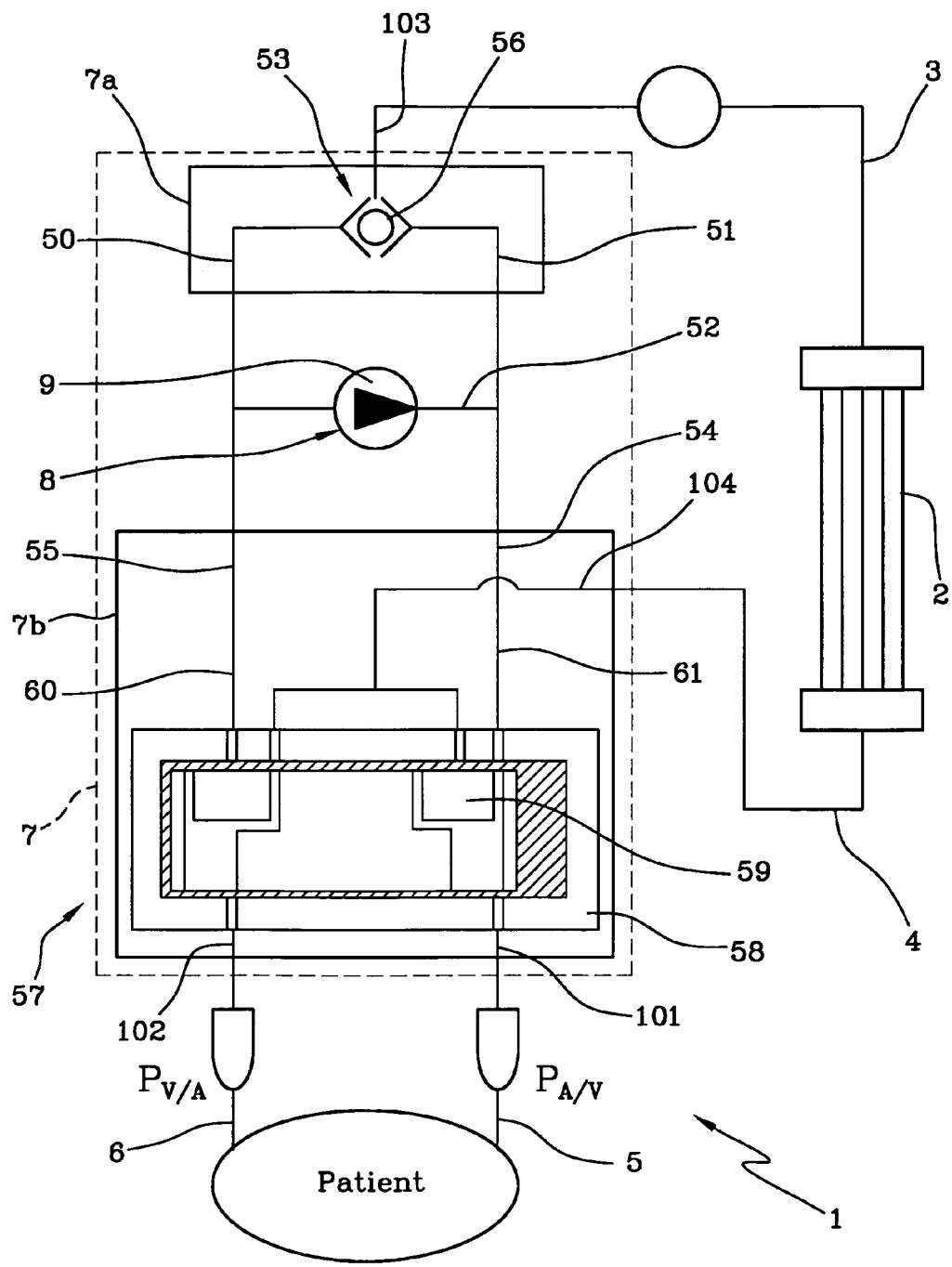
FIG. 7 is a diagrammatic view of a third embodiment of a circuit for extracorporeal blood treatment in accordance with the present invention.

It is apparent that in order to obtain this technical effect, the most varied valve configurations, even different from the example shown in the figures can be utilised. For example, appropriate clamps (of the C-shaped type or still different) can be used, which are capable of engaging a portion of the connecting lines to selectively deform it by squashing so as to obtain interdiction or not to the fluid passage in the various lines thus obtaining the desired rectifying effect. Drive of these clamps can be manual, electromechanical or other. Still alternatively, other appropriate elements can be used to deform the tubes in a preestablished manner so as to obtain blood passage along the desired lines and directions (this is true with respect to all the three embodiments here described; FIGS. 1, 4, 7).

The flow-inverting device 7 referred to in the FIGS. 1-3 is then provided with one-way passage means 13 interposed between at least two accesses 101, 102, 103, 104 to enable one flow in a single direction between said accesses. In the embodiment shown, the one-way passage means 13 is placed at least in one of said connecting lines 14, 15, 16, 17 and in general in each of said connecting lines to enable a flow in a single direction therein.

For example, this one-way passage means 13 can consist of a preestablished number of check valves 18, and in particular of at least one valve 18 for each of the connecting lines 14, 15, 16 and 17.

Obviously more than one check valve can be alternatively provided for each of the above-mentioned lines of the flow-inverting device 7.

Arrangement of these valves 18 enables one fluid passage in the connecting line 14 exclusively from the first access 101 to the third access 103, in the second connecting line exclusively from the fourth access 104 to the first access 101, in the third connecting line 16 exclusively from the fourth access 104 to the second access 102 and in the fourth connecting line 17 exclusively from the second access 102 to the third access 103.

It is well apparent that the one-way passage means 13 can take the most different configurations. The same can be directly integrated into the connecting lines for example, being defined by elastic lips internal to the tube section susceptible of deformation to enable passage along a preestablished direction alone.

Obviously for the above purpose can be also taken into consideration members provided with spring-return elements capable of enabling blood passage in one direction alone and only in the presence of overpressures (this is true also with respect to the second embodiment).

After the above statements from a structural point of view, operation of the circuit for extracorporeal blood treatment (first embodiment) is the following.

In a first work condition of the movement means 8, the peristaltic pump 9 generates a direct flow (arrow 10 in FIG. 2) in which the blood is drawn from the patient's vascular access through the patient-side artery branch 5 and is then moved towards the flow-inverting device 7 reaching the first access 101.

Under this situation the flow pressure is of such a nature that opening of the check valve 18 connected to the first connecting line 14 is allowed thereby causing blood passage to the third access 103.

Simultaneously, the check valves 18 present in the second and fourth connecting lines 15, 17 prevent blood passage to the fourth access 104 and second access 102, respectively. Then the blood flow will take the direction shown by arrow 12 in the unit-side artery branch 3.

The blood flow, once it has passed through the filtering unit 2, will pass through the unit-side vein branch 4 coming close to the fourth access 104 of the flow-inverting device. Here pressure will enable opening of the check valve 18 present in the third connecting line 16 so that the flow can reach the second access 102.

Simultaneously, the check valves 18 present in the second and fourth connecting lines 15, 17 will prevent passage of flow along these lines still due to the pressure differences generated in the device lines.

The flow, once it has reached access 102, will go on along the patient-side vein branch 6 to be then returned to the patient's vascular system. Should, on the contrary, the movement means 8 be disposed in a second work condition by inversion of the thrust direction of the peristaltic pump 9 a reverse flow (denoted by arrow 11 in FIG. 3) would be generated within the circuit, first in the patient-side artery branch 5, i.e. a flow from the flow-inverting device 7 to the patient.

In particular, looking at FIG. 3 it is possible to see that in this second work condition the blood is drawn through the vascular access by the patient-side vein branch 6 until the second access 102 is reached.

Here pressure will enable opening of the check valve 18 present in the fourth connecting line 17 until the third access 103 is reached. Simultaneously, the check valves 18 present in the first and third connecting lines 14, 16 will prevent flowing along these stretches.

The flow, once it has reached the third access 103, will go on in the direction identified in the figure with reference numeral 12 passing through the unit-side artery branch entering the filtering unit 2 and then will go on along its travel through the unit-side vein branch 4 until the fourth access 104 is reached.

Under this situation too, pressure will enable opening of the check valve 18 present in the second connecting line 15 so that the flow can reach the first access 101.

Obviously, the check valve 18 present in the third connecting line 13 will prevent flowing along this stretch. Then from the first access 101 the blood will run through the patient-side artery branch 5 until the patient's vascular access is reached.

Therefore, as it is possible to ascertain by comparing the two different configurations shown in FIGS. 2 and 3, the flow-inverting device 7 is capable of keeping the flow direction 12 in the unit-side artery and vein branches 3, 4 unchanged (in a quite automatic manner and therefore without a manual or human intervention on the inverting device being required), both in the first and in the second work conditions of the peristaltic pump 9.

In other words, by inverting the peristaltic pump 9 the circulation flow of the blood in the patient-side artery and vein branches 5, 6 is inverted, while the circulation flow in the unit-side vein and artery branches 4, 3 keeps unchanged.

In fact, in detail, the inverting device by use of the check valves will behave as if flow-rectifying means were present inside it, which means automatically responds to pressure variations in the patient-side branches due to inversion of the pump 9 to keep the flow in the unit-side branches unchanged.

By contrast according to the second and the third embodiment of the present invention (FIGS. 4-6 and FIGS. 7-9 respectively) it is to be noted that movement means 8 is placed in a different position with respect to the first embodiment.

Indeed in the last two embodiments at least part of the flow-inverting device 7 is interposed in circuit between the movement means 8 (for example the blood pump 9) and the blood treatment unit 2 (vice-versa in the first embodiment the movement means 8 are clearly externally in circuit from said flow inverting device 7).

Both the second and the third embodiment (see in particular FIGS. 4 and 7) are made of a first portion 7a and of a second portion 7b and the peristaltic pump 9 is, of both cases, interposed between these two parts.

In particular the first portion 7a presents the above mentioned third access 103 directly connected with the unit-side artery branch 3 as well as a main and an auxiliary inlet 50, 51 both in fluid communication with said movement means 8.

As can be seen in FIGS. 5, 6, 8 and 9 a blood flow always runs out from the third access 103 so as blood can enter the filter 2. This happens in the first work condition of the movement means 8, but also in the second work condition of the same movement means 8, condition which is obtained by the reversal of the thrust direction of the peristaltic pump 9.

Figure 5:
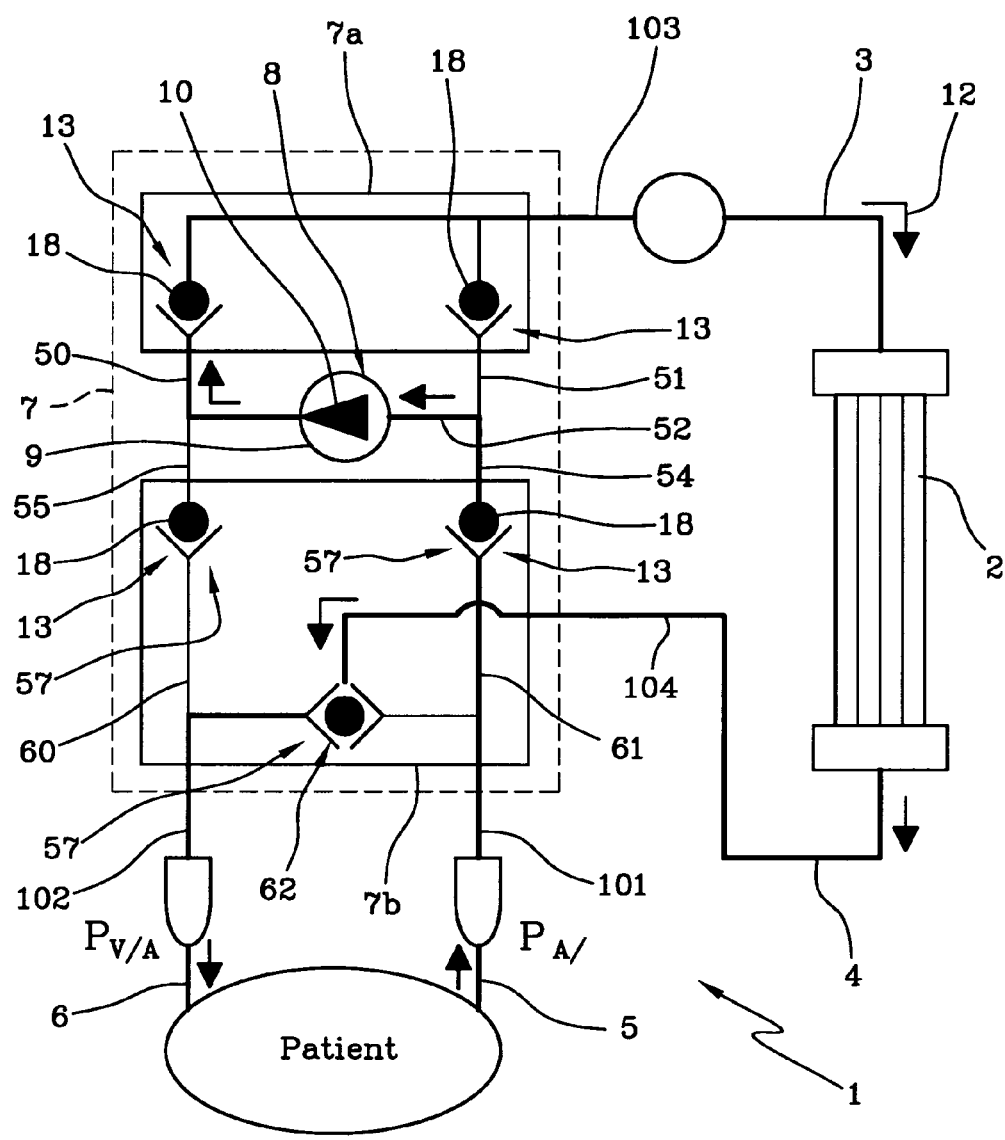
FIG. 5 shows the circuit of FIG. 4 in a first direct operating condition.
Figure 8:
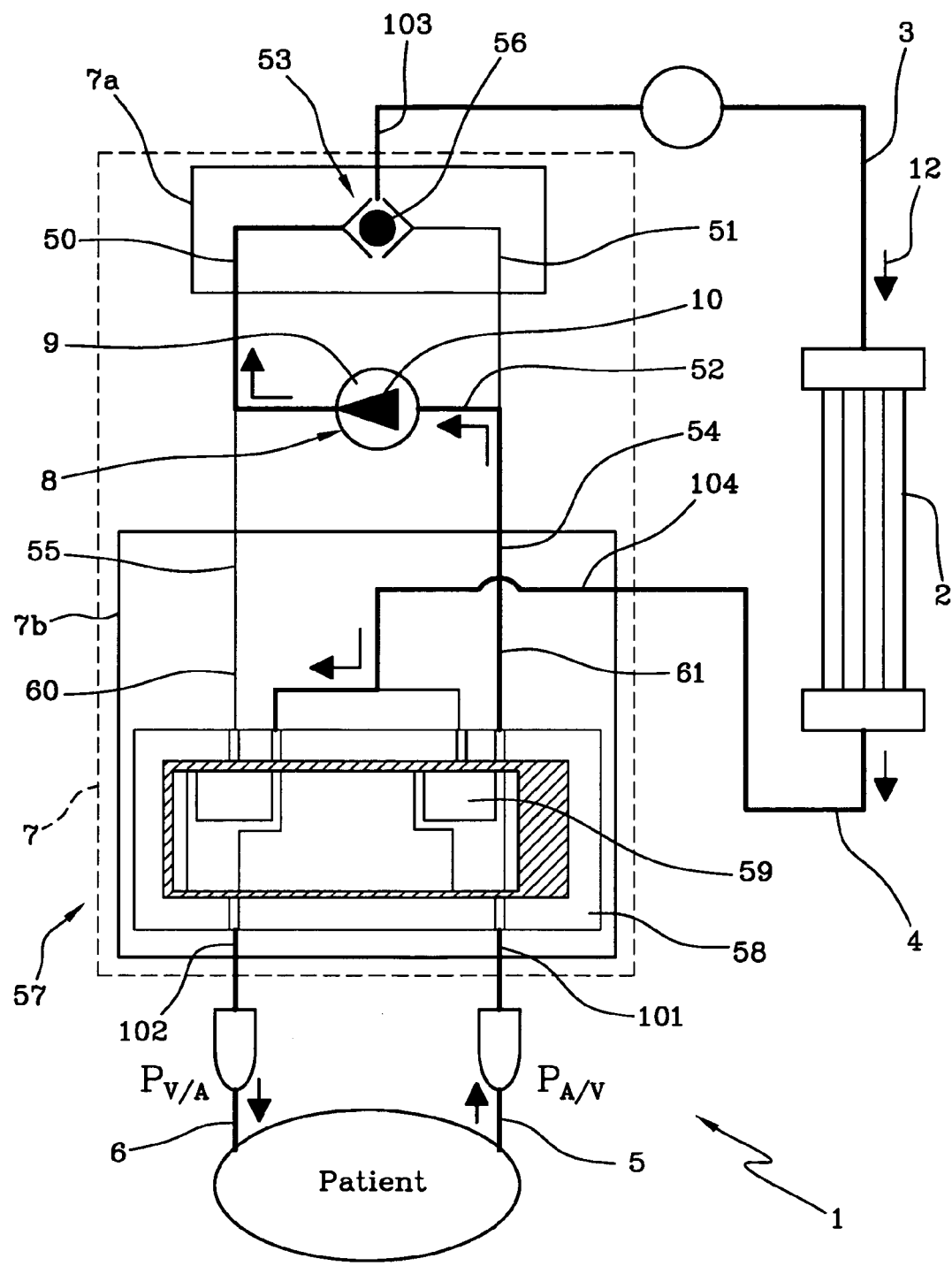
FIG. 8 shows the circuit of FIG. 7 in a first direct operating condition.

In case of direct flow 10 of the peristaltic pump 9 the blood flow is allowed in the main inlet 50 towards the third access 103 (see FIGS. 5 and 8).

In the same condition the blood flow is precluded in the auxiliary inlet 51.

Following reversal of the thrust direction of the peristaltic pump 9, a reverse flow (denoted by arrow 11 in FIGS. 6 and 9) would be generated within the circuit and a blood flow will be allowed in the auxiliary inlet 51 towards the third access 103 while being precluded in the main inlet 50.

The above described hydraulic configuration is obtained in the second embodiment by the use of a one-way passage means 13 interposed between the main and/or the auxiliary inlets 50, 51 and the third access 103.

Figure 6:
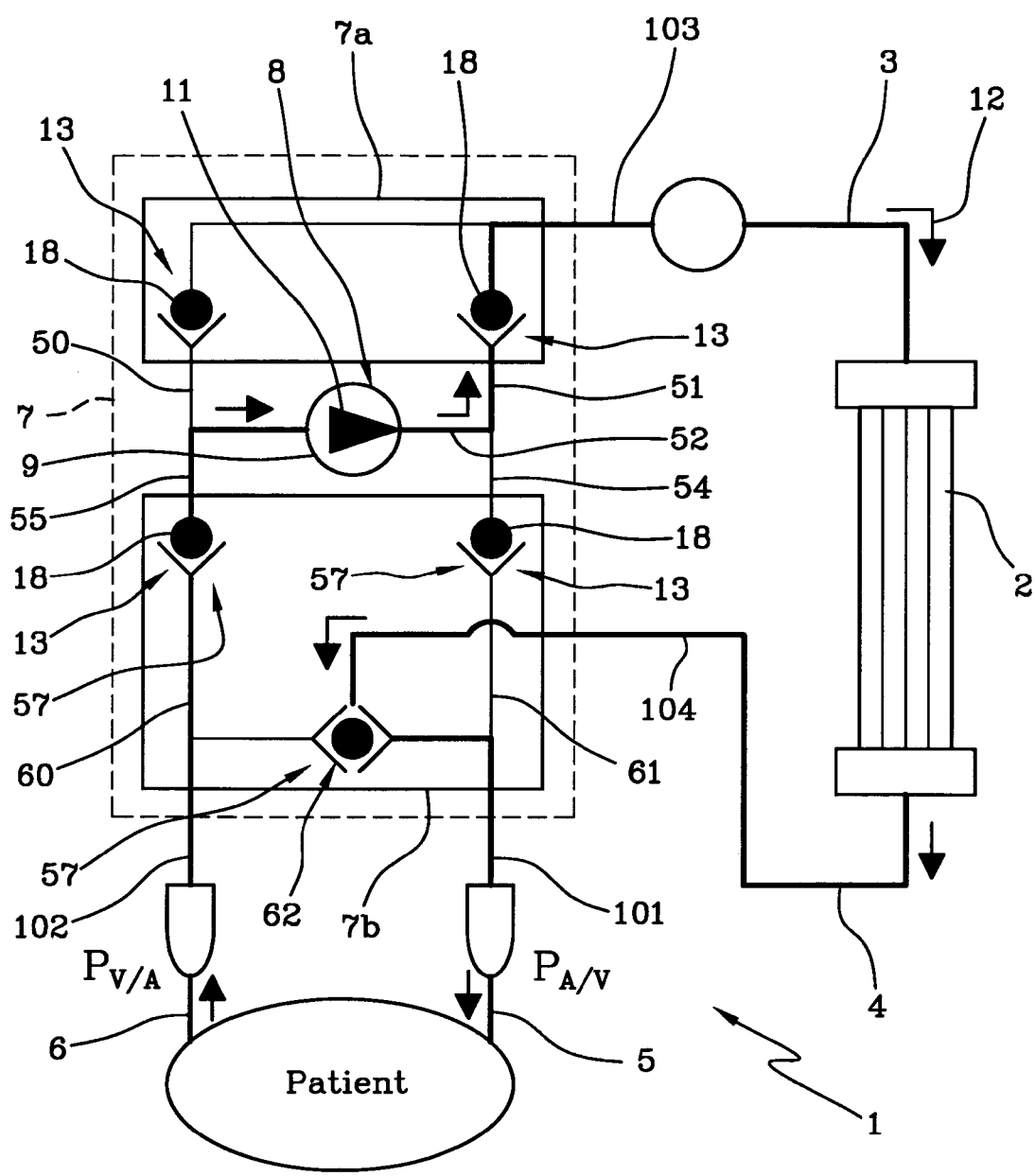
FIG. 6 shows the circuit in FIG. 4 in a second inverted operating condition.

As can be seen in FIGS. 5 and 6 the one-way passage means 13 may be defined by at least one check valve 18.

Obviously more than one valve for each line can be used and also different and equivalent solution may be used as previously described.

Figure 9:
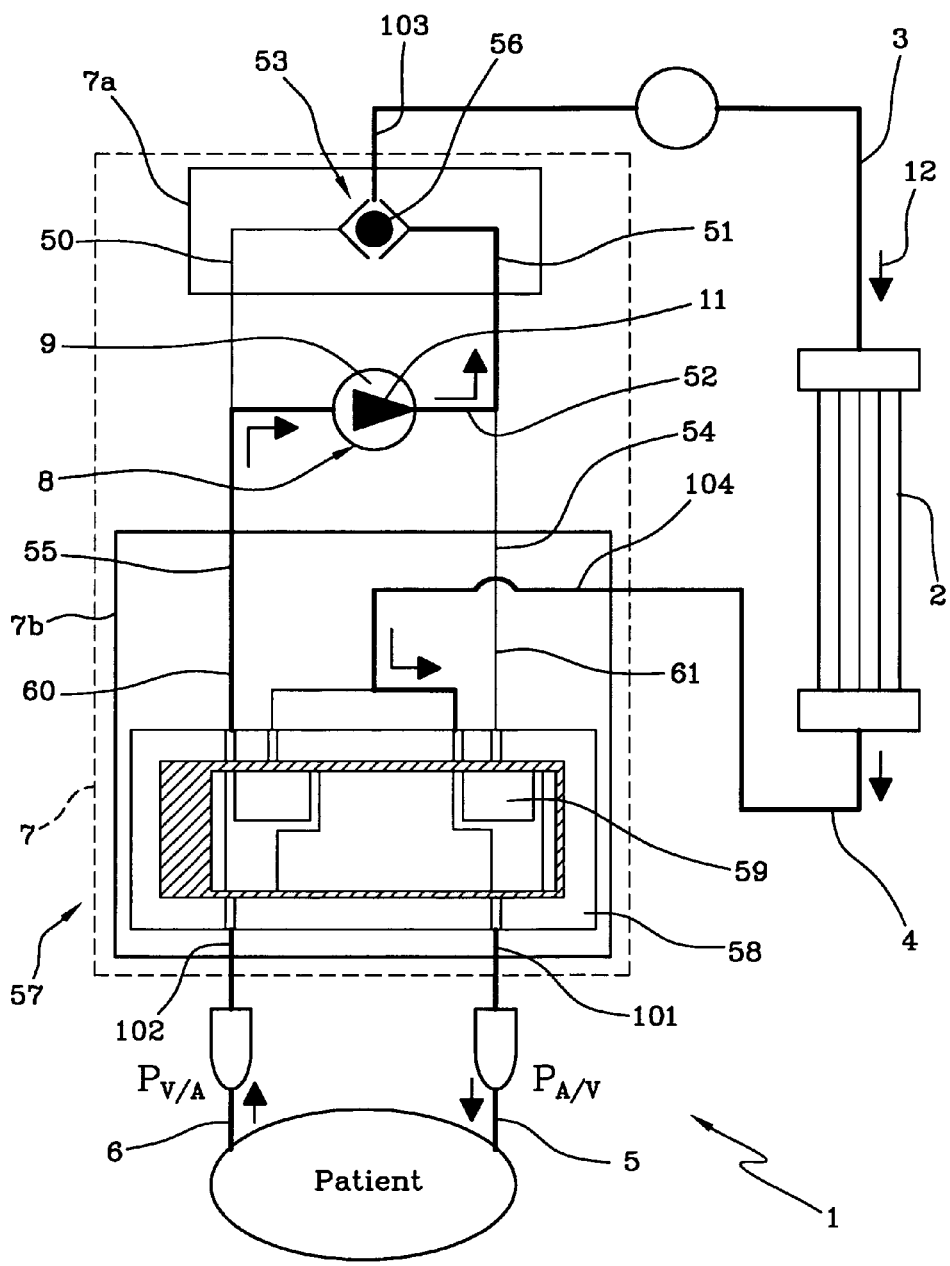
FIG. 9 shows the circuit in FIG. 7 in a second inverted operating condition.

In the solution shown in FIGS. 8 and 9 at least a two inlets-one outlet means 53 may be used.

Such means 53 is capable of receiving a blood flow either from one or the other inlet 50, 51 and to anyway allow a blood flow in a one-way direction in the outlet 103.

For example a three-way valve 56 directly connected with the main and the auxiliary inlets 50, 51 and the third access 103 may be used as shown is FIGS. 8 and 9.

Figure 10A:
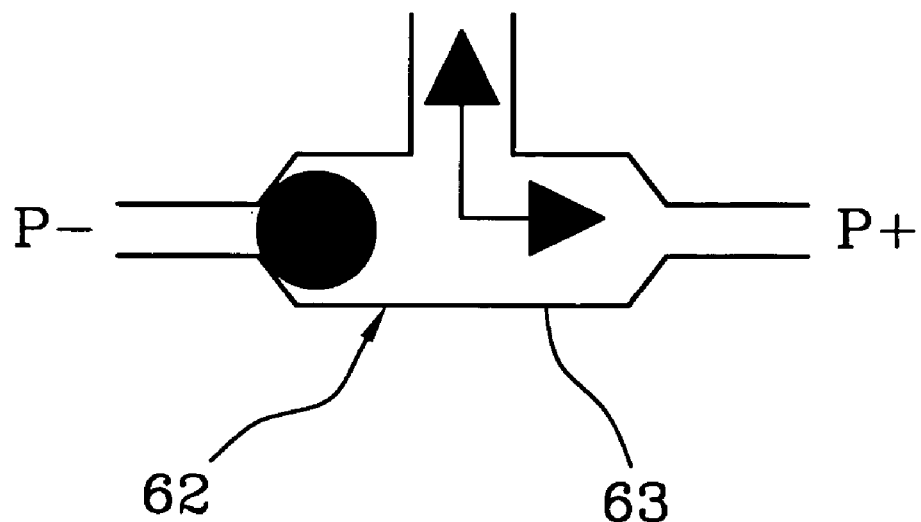
FIGS. 10a and 10b shows a three-way check valve in two different working conditions.
Figure 10B:
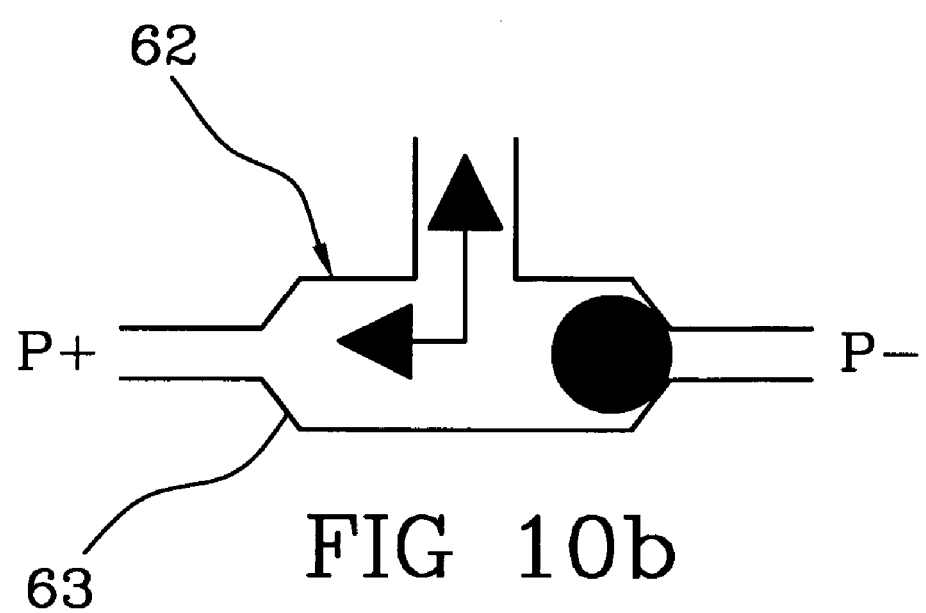

From a structural point of view such a three-way check valve may be made as shown in FIGS. 10a and 10b; the fluid may come from anyone of the open passages towards one of the two other channels.

Only a passage from a left inlet to the right inlet and vice-versa is always precluded.

Particularly the pressure difference over the outputs (inputs) determines which output (input) will be opened and which will be closed as clearly understood by the skilled person.

Obviously other suitable hydraulic geometries or structures may be used in order to obtain the same technical effect (i.e. direct inlet/output blood passage).

A second portion 7b of both the second and the third embodiments presents at least a first, a second and a fourth access 101, 102, 104 as well as a main and an auxiliary outlets 54, 55.

In the first work condition of the movement means 8, a blood flow from first access 101 towards the main outlet 54 is allowed, while a blood flow is precluded in the auxiliary outlet 55 (see in this respect FIGS. 5 and 8).

By contract in the second work condition of the movement means 8 (FIGS. 6 and 9) the blood flow is allowed from the second access 102 towards the auxiliary outlet 55 while being precluded in the main outlet 54.

Structurally speaking, the second portion 7b comprises two lines 60, 61; the first line 60 connects the second access 102 with the auxiliary outlet 55 which is in turn directly connected with the main inlet 50 of the first portion 7a.

The second line 61 connects the first access 101 to the main outlet 54 which is in turn directly connected with the auxiliary inlet 51 of the first portion 7a.

Both the second and the third embodiment of the flow-inverting device 7 show a blood flow coming from the filter 2 through the unit-side vein branch 4 which is directed, in the first work condition of the movement means 8, towards the second access 102, while it is directed, in the second work condition of the movement means, towards the first access 101.

In other words the thrust inversion of the peristaltic pump 9 does not affect the blood flow in the fourth access 104 while it inverts blood flow in the first and second accesses 101, 102.

In other words the second portion 7b comprises means 57 for allowing, in the first work condition, a blood flow from the first access 101 to the main outlet 54 and from the fourth access 104 towards the second access 102 and for allowing, in the second work condition, a blood flow from the second access 102 to the auxiliary outlet 55 and from the fourth access 104 towards the first access 101.

In the second embodiment said means 57 comprises at least one-way passage means 13 interposed between main and/or auxiliary outlet 54, 55 and the first and/or second access 101, 102.

As can be seen at least one check valve 18 is placed on the first line 60 and at least one check valve 18 is placed on the second line 61.

Moreover means 57 of the second embodiment comprises at least a one inlet-two outlets means 62 capable of receiving a blood flow from the fourth access 104 and to allow a blood flow towards the second access 102 or towards the first access 101 selectively.

For example the three-way valve 63 shown in FIGS. 10a and 10b may be used.

In particular such a three-way valve will be placed on a line directly connecting the previously described first line 60 and second line 61; the third inlet of the three-way valve is directly connected with the fourth access 104.

It is clear that the second embodiment as well as the first embodiment automatically allows the correct blood flow in the circuit as soon as the peristaltic pump is activated in its direct or inverted condition.

By contrast the third embodiment of the flow-inverting device 7 has means 57 which comprises a valve 58 (for example a slide valve) having a body 59 movable between at least a normal portion allowing a blood flow from the fourth 104 to the second access 102 and from the first access 101 to the main outlet 54 and a reversed position allowing a blood flow from the fourth 104 to the first access 101 and from the second access 102 to the auxiliary outlet 55.

In detail the movable body 59 is internally defined in a chamber of the slide valve and may translate from normal to reserved position and vice-versa.

In the pictures (FIGS. 7-9) the valve consists of a slide that connects different outlets and inlets depending on if the slide is in the left or in the right position.

Obviously the slide shifts position each time the direction of the pump is changed.

The movable body 59 presents peculiar internal paths which allow the above mentioned blood flows.

Obviously in this last embodiment the slide valve may be controlled electrically or mechanically by the direction of the blood pump but obviously other way of controlling such a valve may be used.

Finally as can be seen from FIGS. 4 to 9 it is to be noted that the peristaltic pump of the movement means 8 is placed on a line 52 directly connecting the main and the auxiliary outlets 54, 55 and also directly connecting the main and the auxiliary inlets 50, 51.

The invention achieves important advantages.

First of all the device of the invention enables the flow direction within the blood treatment unit to be kept constant, irrespective of the direct or reverse operating conditions of the peristaltic blood pump.

On the other hand, the device is able to allow the above operation in a quite automatic manner and without any intervention by an operator being required.

With reference to the embodiment shown, use of suitably positioned check valves allows a very simple and cheap circuit to be obtained.

In addition, due to the absence of a manual or electromechanical intervention for maintenance of the flow conditions, the device is very reliable and the risks of malfunction are very reduced.

Notice that though in the enclosed drawings lines 3,4,5,6 appear to have a certain length relative to the remaining components, the dimensions shown are to be understood by way of example only and not as limiting features. Moreover said lines may be obtained by means of conventional deformable tubes or, alternatively, may be obtained with rigid structures.

The device 7 itself could be obtained in a cassette like rigid structure, integrating the venous and arterial bubble traps if any and/or the dialyzer.

The connections between the treatment unit blood inlet and blood outlet with ports 101 and 103 (i.e. the unit-side branches) could be minimized in length and even reduced to direct connections with the treatment unit.

What is claimed is:

1. A circuit for extracorporeal blood treatment comprising:
    at least one blood treatment unit;
    at least one unit-side artery branch and at least one unit-side vein branch connected with the treatment unit;
    at least one patient-side artery branch and at least one patient-side vein branch designed to be put into fluid communication with a patient's vascular access;
    at least one device for flow inversion in connection with said unit-side artery branch and vein branch and with said patient-side artery branch and vein branch, said inverting device allowing at least one direct operating condition of fluid connection between the patient-side artery branch and the unit-side artery branch and an inverted operating condition of fluid connection between the patient-side vein branch and the unit-side artery branch; and
    movement means to generate a flow in said patient-side artery and vein branches and said unit-side artery and vein branches,
    wherein at least part of said flow-inverting device is interposed in circuit between said movement means and blood treatment unit and is capable of maintaining the flow direction in the unit-side artery and vein branches unchanged both in its direct operating condition and its inverted operating condition, said flow-inverting device having at least four accesses, a first access being brought into fluid connection with the patient-side artery branch, a second access being brought into fluid connection with the patient-side vein branch, a third access being brought into fluid connection with the unit-side artery branch, a fourth access being brought into fluid connection with the unit-side vein branch, the first access being selectively in fluid communication either with the third access or with the fourth access and the second access being selectively in fluid communication either with the fourth access or with the third access; and one-way passage means interposed between at least two of said accesses to enable flowing in one direction alone between said two accesses.

2. A circuit as claimed in claim 1, wherein the flow-inverting device comprises at least four connecting lines of the accesses, the first connecting line bringing the first access into fluid communication with the third access, the second connecting line bringing the first access into fluid communication with the fourth access, the third connecting line bringing the second access into fluid communication with the fourth access, the fourth connecting line bringing the second access into fluid communication with the third access.

3. A circuit as claimed in claim 2, wherein the one-way passage means is placed in at least one of said connecting lines.

4. A circuit as claimed in claim 3, wherein the one-way passage means is placed in each of said connecting lines to enable flowing in one direction alone in each of said lines.

5. A circuit as claimed in claim 4, wherein the one-way passage means allows a fluid passage in the connecting line exclusively from the first access to the third access.

6. A circuit as claimed in claim 4, wherein the one-way passage means allows a fluid passage in the second connecting line exclusively from the fourth access to the first access.

7. A circuit as claimed in claim 4, wherein the one-way passage means allows a fluid passage in the third connecting line exclusively from the fourth access to the second access.

8. A circuit as claimed in claim 4, wherein the one-way passage means allows a fluid passage in the fourth connecting line exclusively from the second access to the third access.

9. A circuit as claimed in claim 4, wherein the one-way passage means in the direct operating condition of the inverting device allows a fluid passage from the patient-side artery branch through the first access and to the third access, then through the unit-side artery branch into the blood treatment unit and then a fluid passage through the unit-side vein branch and to the fourth access and therefrom through the third connecting line to the second access and then through the patient-side vein branch to the patient itself.

10. A circuit as claimed in claim 4, wherein the one-way passage means in the inverted operating condition of the inverting device allows a fluid passage from the patient-side vein branch through the second access to the third access, from the third access through the unit-side artery branch and then through the blood treatment unit, then from the unit-side vein branch through the fourth access to the first access and then through the patient-side artery branch to the patient itself.

11. A circuit as claimed in claim 2, wherein the one-way passage means comprises at least one check valve for each of said connecting lines.

12. A circuit as claimed in claim 1, wherein the one-way passage means comprises at least one check valve.

* * * * *